United States Patent [19]

Hanson et al.

[11] Patent Number: 4,902,706
[45] Date of Patent: Feb. 20, 1990

[54] AMINOALKYLAMINOCARBONYL AMINODIOL AMINO ACID DERIVATIVES AS ANTIHYPERTENSIVE AGENTS

[75] Inventors: Gunnar J. Hanson, Skokie; John S. Baran, Winnetka, both of Ill.

[73] Assignee: G. D. Searle & Co., Chicago, Ill.

[21] Appl. No.: 214,234

[22] Filed: Jul. 1, 1988

[51] Int. Cl.$^4$ .................. A61K 31/415; C07D 233/64
[52] U.S. Cl. ..................................... 514/400; 548/344
[58] Field of Search ........................ 548/344; 514/400

[56] References Cited

FOREIGN PATENT DOCUMENTS

| | | |
|---|---|---|
| 128762 | 12/1984 | European Pat. Off. . |
| 172346 | 2/1986 | European Pat. Off. . |
| 172347 | 2/1986 | European Pat. Off. . |
| 181110 | 5/1986 | European Pat. Off. . |
| 189203 | 7/1986 | European Pat. Off. . |
| 200406 | 12/1986 | European Pat. Off. . |
| 216539 | 4/1987 | European Pat. Off. . |
| 229667 | 7/1987 | European Pat. Off. . |
| 300189 | 1/1989 | European Pat. Off. . |
| 307837 | 3/1989 | European Pat. Off. . |
| WO87/04349 | 7/1987 | PCT Int'l Appl. . |

OTHER PUBLICATIONS

Umezawa et al, *J. Antibiot.* (Tokyo), 23:259–262 (1970).
Gross et al, *Science*, 175, 656 (1971).
Boger et al, *Nature*, 303, 81 (1983).
Kokubu et al, *Biochim. Biophys. Res. Commun.*, 118, 929 (1984).
Fehrentz et al, *FEBS Lett.*, 167, 273 (1984).
Hanson et al, *Biochm. Biophys. Res. Comm.*, 132:155–161 (1985), 146:959–963 (1987).
Marshall, *Federation Proc.*, 35:2494–2501 (1976).
Burton et al, *Proc. Natl. Acad. Sci. USA*, 77:5476–5479 (1980).
Suketa et al, *Biochemistry*, 14:3188 (1975).
Swales, *Pharmac. Ther.*, 7:173–201 (1979).
Kokubu et al, *Nature*, 217:456–457 (1968).
Matsushita et al, *J. Antibiotics*, 28:1016–1018 (1975).
Lazar et al, *Biochem. Pharma.*, 23:2776–2778 (1974).
Miller et al, *Biochem. Pharma.*, 21:2941–2944 (1972).
Haber, *Clinical Science*, 59:7s–19s (1980).
Rich et al, *J. Org. Chem.*, 43:3624 (1978).
Rich et al, *J. Med. Chem.*, 23:27 (1980).
Haber, *Clin. and Exper. Hyper.*, A5(7&8), 1193 (1983).

*Primary Examiner*—Richard A. Schwartz
*Attorney, Agent, or Firm*—J. Timothy Keane; Paul D. Matukaitis

[57] ABSTRACT

Non-peptidyl compounds characterized generally as aminoalkylaminocarbonyl aminodiol derivatives of amino acids are useful as renin inhibitors for the treatment of hypertension.

4 Claims, No Drawings

AMINOALKYLAMINOCARBONYL AMINODIOL AMINO ACID DERIVATIVES AS ANTIHYPERTENSIVE AGENTS

FIELD OF THE INVENTION

Renin-inhibiting compounds are known for control of hypertension. Of particular interest herein are non-peptidyl compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23:259–262 (1970)]. This peptide, known as pepstatin, was found to reduce blood pressure in vivo after the the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger, et al, *Nature*, 303, 81 (1983)]; high molecular weight peptides are generally considered undesirable as drugs because gastrointestinal absorption is impaired and plasma stability is compromised.

Short peptide aldehydes have been reported as renin inhibitors [Kokubu et al, *Biochim. Biophys. Res. Commun.*, 118, 929 (1984); Castro et al, FEBS Lett., 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glycol-containing compounds as renin inhibitors [also see Hanson et al, *Biochm. Biophys. Res. Comm.*, 132:155-161 (1985), 146:959-963 (1987)]. EP Appl. #181,110, published May 14, 1986, describes dipeptide histidine derivatives as renin inhibitors. EP Appl. #189,203, published July 30, 1986, describes peptidylaminodiols as renin inhibitors. EP Appl. #200,406, published Dec. 10, 1986, describes alkylnaphthylmethylpropionyl-histidyl aminohydroxy alkanoates as renin inhibitors. EP Appl. #216,539, published April 1, 1987, describes alkylnaphthylmethylpropionyl aminoacyl aminoalkanoate compounds as renin inhibitors orally administered for treatment of renin-associated hypertension. EP Appl. #229,667 describes acyl α-aminoacyl aminodiol compounds having a piperazinylcarbonyl or an alkylaminoalkylcarbonyl terminal group at the N-amino acid terminus, such as 2(S)-[(1-piperazinyl)carbonyl]oxy]-3-phenylpropionyl}- Phe-His amide of 2(S)-amino-1-cyclohexyl-3(R),4(S)-dihydroxy-6-methylheptane For other articles describing previous efforts to devise renin inhibitors, see Marshall, *Federation Proc.*, 35: 2494–2501 (1976); Burton et al, *Proc Natl. Acad. Sci. USA*, 77: 5476–5479 (1980); Suketa et al, *Biochemistry*, 14: 3188 (1975;) Swales, *Pharmac. Ther.*, 7: 173–201 (1979); Kokubu et al, *Nature*, 217: 456–457 (1986); Matsushita et al, *J. Antibiotics*, 28: 1016–1018 (1975); Lazar et al, *Biochem. Pharma.*, 23: 2776–2778 (1974); Miller et al., *Biochem. Pharma* , 21: 2941–2944 (1972); Haber, Clinical Science, 59: 7s–19s (1980); Rich et al, *J. Org. Chem.*, 43: 3624 (1978); *J. Med. Chem.*, 23: 27 (1980); especially Haber, *Clin. and Exper. Hyper.*, A5(7& 8), 1193 (1983); and European Patent Applications 172346A and 172347A published Feb. 26, 1986.

DESCRIPTION OF THE INVENTION

Non-peptidyl aminoalkylaminocarbonyl aminodiol amino acid derivatives having utility as renin inhibitors for treatment of hypertension in mammals constitute a family of compounds of general Formula I:

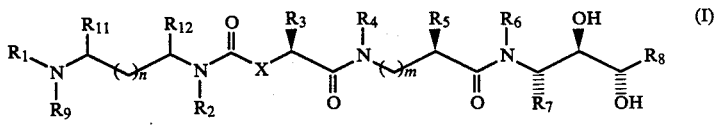

wherein X is selected from oxygen atom, methylene and $NR_{10}$ with $R_{10}$ selected from hydrido, alkyl and benzyl; wherein each of $R_1$ and $R_9$ is a group independently selected from hydrido, alkyl, cycloalkyl, alkylacyl, haloalkylacyl, phenyl, benzyl, naphthyl and naphthylmethyl, any one of which groups having a substitutable position may be optionally substituted with one or more radicals selected from alkyl, alkoxy, alkenyl, alkynyl, halo, haloalkyl, cyano and phenyl; wherein $R_1$ and $R_9$ may be taken together to form an alkylene chain or an alkenylene chain or a heterocylic group having one or two hetero atoms selected from nitrogen, oxygen and sulfur to form a cyclic structure having 4 to 10 ring members; wherein $R_2$ is selected from hydrido, alkyl, alkylaminoalkyl, alkylacylaminoalkyl, benzyl and cycloalkyl; wherein $R_3$ is selected from alkyl, acylaminoalkyl, phenylalkyl, naphthylmethyl, aryl and heterocyclicalkyl, wherein the aromatic portion of any of said phenylalkyl, naphthylmethyl, aryl and heterocyclicalkyl may be substituted by one or more halo or alkyl or by both; wherein each of $R_4$ and $R_6$ is independently selected from hydrido, alkyl, benzyl and cycloalky; wherein $R_7$ is selected from substituted or unsubstituted cycloalkyl, phenyl, cycloalkylalkyl and phenylalkyl, any one of which may be substituted with one or more groups selected from alkyl, alkoxy, halo, haloalkyl, alkenyl, alkynyl and cyano; wherein $R_8$ is selected from hydrido, alkyl, haloalkyl, alkylcycloalkyl, alkylcycloalkenyl and alkoxycarbonyl; wherein each of $R_{11}$ and $R_{12}$ is independently selected from hydrido, alkyl, alkylaminoalkyl and phenyl; and wherein m is zero or one and n is a whole number selected from one through five;

with the proviso that where m is zero, then $R_5$ is selected from hydrido, alkyl, benzyl, cycloalkyl, cycloalkylalkyl, hydroxyalkyl, alkoxyalkyl, alkylthioalkyl, heterocyclicalkyl, sulfonylheterocyclicalkyl and acylheterocyclicalkyl; and with the further proviso that when m is one, then $R_5$ is selected from hydrido, alkyl, benzyl, cycloalkyl, cycloalkylalkyl, alkoxyalkyl, alkylthioalkyl and imidazolemethyl.

Two distinct families of renin-inhibiting compounds are specified within Formula I, namely, those families being defined by the values of m. A first family of compounds consists of those α-amino acid derivatives defined by the condition where m is zero. A second family of compounds consists of those β-amino acid derivatives defined by the condition where m is one.

A preferred family of compounds consists of those compounds of Formula I wherein X is selected from oxygen atom, methylene and $NR_{10}$ with $R_{10}$ selected from hydrido, alkyl and benzyl; wherein each of $R_1$ and $R_9$ is independently selected from hydrido, lower alkyl, cycloalkyl, phenyl and benzyl; wherein $R_1$ and $R_9$ may be taken together to form an alkylene or alkenylene chain to form a cyclic structure having 5 to 7 ring members; wherein each of $R_2$, $R_4$ and $R_6$ is independently selected from hydrido and alkyl; wherein $R_3$ is selected from phenylalkyl, naphthylmethyl, pyridylmethyl, pyridylethyl and pyridylpropyl; wherein $R_7$ is selected from substituted or unsubstituted cyclohexylmethyl and benzyl, either one of which may be substituted with one or more groups selected from alkyl, alkoxy, halo and haloalkyl; wherein $R_8$ is selected from hydrido, ethyl, n-propyl, n-butyl, isobutyl and fluoroalkyl; wherein each of $R_{11}$ and $R_{12}$ is independently selected from hydrido and lower alkyl; wherein m is zero or one and n is a whole number selected from one through five; or a pharmaceutically-acceptable salt thereof;

with the proviso that where m is zero, then $R_5$ is selected from hydrido, alkyl, benzyl, cycloalkyl, cycloalkylalkyl, imidazolemethyl, imidazoleethyl, thiazolemethyl, pyridylmethyl, sulfonylimidazolemethyl acylimidazolemethyl; and with the further proviso that when m is one, then $R_5$ is selected from hydrido, alkyl and imidazolemethyl.

A further preferred family of compounds consists of those compounds of Formula I wherein X is selected from oxygen atom, methylene and $NR_{10}$ with $R_{10}$ selected from hydrido, alkyl and benzyl; wherein each of $R_1$ and $R_9$ is independently selected from hydrido, methyl and ethyl; wherein $R_1$ and $R_9$ may be taken together to form an alkylene or alkenylene chain to form a cyclic structure having 6 ring members; wherein each of $R_2$, $R_4$ and $R_6$ is hydrido; wherein $R_3$ is selected from benzyl, phenethyl, phenpropyl, pyridylmethyl and 2-pyridylethyl; wherein $R_7$ is cyclohexylmethyl; wherein $R_8$ is selected from ethyl, n-propyl and isobutyl; wherein each of $R_{11}$ and $R_{12}$ is independently selected from hydrido and methyl; wherein m is zero or one and n is a whole number selected from one through five; or a pharmaceutically-acceptable salt thereof;

with the proviso that where m is zero, then $R_5$ is selected from imidazolemethyl, thiazolemethyl and isobutyl; and with the further proviso that when m is one, then $R_5$ is methyl or ethyl.

A more preferred family of compounds consists of those compounds of Formula I wherein X is selected from oxygen atom, methylene and $NR_{10}$ with $R_{10}$ selected from hydrido and methyl; wherein each of $R_1$ and $R_9$ is independently selected from hydrido, lower alkyl and benzyl; wherein $R_1$ and $R_9$ may be taken together to form an alkylene chain to form a cyclic structure having 6 ring members; wherein each of $R_2$, $R_4$ and $R_6$ is hydrido; wherein $R_3$ is selected from benzyl, phenethyl, pyridylmethyl and 2-pyridylethyl; wherein $R_7$ is cyclohexylmethyl; wherein $R_8$ is isobutyl; wherein each of $R_{11}$ and $R_{12}$ is hydrido; wherein m is zero or one and n is a whole number selected from one through five; or a pharmaceutically-acceptable salt thereof; with the proviso that where m is zero, then $R_5$ is selected from imidazolemethyl, thiazolemethyl and isobutyl; and with the further proviso that when m is one, then $R_5$ is methyl or ethyl.

A particularly preferred family of compounds consists of those compounds of Formula I wherein X is selected from oxygen atom and methylene; wherein each of $R_1$ and $R_9$ is independently selected from hydrido, ethyl and methyl; wherein each of $R_2$, $R_4$ and $R_6$ is hydrido; wherein $R_3$ is selected from benzyl, phenethyl, pyridylmethyl and 2-pyridylethyl; wherein $R_7$ is cyclohexylmethyl; wherein $R_8$ is isobutyl; wherein each of $R_{11}$ and $R_{12}$ is hydrido; wherein m is zero or one and n is a whole number selected from one through five; or a pharmaceutically-acceptable salt thereof; with the proviso that where m is zero, then $R_5$ is selected from imidazolemethyl, thiazolemethyl and isobutyl; and with the further proviso that when m is one, then $R_5$ is methyl or ethyl.

A more particularly preferred family of compounds consists of those compounds of Formula I wherein X is selected from oxygen atom and methylene; wherein each of $R_1$ and $R_9$ is a group independently selected from hydrido and methyl; wherein each of $R_2$, $R_4$ and $R_6$ is hydrido; wherein $R_3$ is selected from benzyl, phenethyl, pyridylmethyl and 2-pyridylethyl; wherein $R_7$ is cyclohexylmethyl; wherein $R_8$ is isobutyl; wherein each of $R_{11}$ and $R_{12}$ is hydrido; wherein m is zero or one and n is a whole number selected from one through three; or a pharmaceutically-acceptable salt thereof; with the proviso that where m is zero, then $R_5$ is selected from imidazolemethyl and isobutyl; and with the further proviso that when m is one, then $R_5$ is methyl or ethyl.

A most preferred family of compounds of Formula I consists of the following compounds:

O-N-[2-(N,N-dimethylamino)ethyl]-N-methylaminocarbonyl-3-L-phenyllactyl-L-histidineamide of (2S,3R,4S)-2-amino-1-cyclohexyl-3,4-dihydroxy-6-methylheptane;

O-N-[2-(N-methylamino)ethyl]-N-methylaminocarbonyl}-3-L-phenyllactyl-L-histidineamide of (2S,3R,4S)-2-amino-1-cyclohexyl-3,4-dihydroxy-6-methylheptane;

O-{N-[2-(N-methylamino)ethyl]-N-methylaminocarbonyl}-3-L-phenyllactyl-L-leucineamide of (2S,3R,4S)-2-amino-1-cyclohexyl-3,4-dihydroxy-6-methylheptane;

O-N-[2-(N,N-dimethylamino)ethyl]-N-methylaminocarbonyl}-3-L-phenyllactyl-L-leucineamide of (2S,3R,4S)-2-amino-1-cyclohexyl-3,4-dihydroxy-6-methylheptane;

O-{N-[2-(N,N-dimethylamino)ethyl]-N-methylaminocarbonyl}-3-L-phenyllactyl-α-(R)-methyl-β-alanineamide of (2S,3R,4S)-2-amino-1-cyclohexyl-3,4-dihydroxy-6-methylheptane;

O-{N-[2-(N,N-dimethylamino)ethyl]-N-methylaminocarbonyl}-3-L-homophenyllactyl-α-(R)-methyl-β-alanineamide of (2S,3R,4S)-2-amino-1-cyclohexyl-3,4-dihydroxy-6-methylheptane;

O-N-[2-(N,N-dimethylamino)ethyl]-N-methylaminocarbonyl}-3-L-homophenyllactyl-α-(R)-ethyl-β-alanineamide of (2S,3R,4S)-2-amino-1-cyclohexyl-3,4-dihydroxy-6-methylheptane; and 3-N-[2-(N,N-dimethylamino)ethyl]-N-methylaminocarbonyl}-2-(R)-(2-phenylethyl)-propionyl-α-(R)-ethyl-β-alanineamide of (2S,3R,4S)-2-amino-1-cyclo-hexyl-3,4-dihydroxy-6-methylheptane;

3-{N-[2-(N-piperdino)ethyl]-N-methylaminocarbonyl}-3-L-phenyllactyl-L-histidineamide of (2S,3R,4S)-2-amino-1-cyclohexyl-3,4-dihydroxy-6-methylheptane;

3-N-[2-(N-piperdino)ethyl]-N-methylaminocarbonyl}-2-(R)-(2-phenylethyl)-propionyl-α-(R)-ethyl-β-alanineamide of (2S,3R,4S)-2-amino-1-cyclohexyl-3,4-dihydroxy-6-methylheptane.

Unless otherwise described, the chemical groups recited herein shall have meanings as follows: "lower alkyl" means alkyl radicals containing one to about 10 carbon atoms in a linear or branched configuration, examples of which include methyl, ethyl, n-propyl, isopropyl, n-butyl, sec-butyl, iso-butyl, tert-butyl, n-pentyl, neopentyl, n-hexyl, 1-methylhexyl, n-heptyl, 2-ethylheptyl, n-octyl, 3-propyloctyl, n-nonyl, 4-butylnonyl, n-decyl and the like. "Haloalkyl" means alkyl radicals substituted at one or more substitutable positions with one or more halo groups. Preferred haloalkyl group are those provided by lower alkyl radicals substituted at least at one position with one, two or three halo groups such as fluoro or chloro, a specific example of which is trifluoromethyl. "Alkylcycloalkyl" means a cyclized alkyl having from four to about nine ring carbon atoms, any one or more of the substitutable ring carbon atoms being substituted with an alkyl group, preferably a lower alkyl group. "Alkoxycarbonyl" means an oxycarbonyl radical having an alkyl, preferably lower alkyl, group attached to the oxygen atom. "Aryl" means an aromatic hydrocarbon radical provided by a homocyclic or heterocyclic ring system, such as phenyl, naphthyl, and pyridyl. "Acyl" means a carbonyl radical attached to a hydrocarbon moiety, typically an alkyl or lower alkyl group. "Heterocyclicalkyl" means a cyclized group having three to about ten ring members, of which one to about three of such ring members is a hetero atom selected from oxygen, nitrogen and sulfur, with the remaining ring members being carbon atoms and such cyclized group being fully unsaturated, or partially saturated, or fully saturated.

Based upon the foregoing, the meanings of the following terms should be readily discernible, namely, "acylaminoalkyl", "cycloalkyl", "cycloalkylalkyl", "phenylalkyl" and "alkoxy".

Compounds of Formula I have at least five asymmetric carbons. Such compounds whether in their pure isomer form or as diastereomeric mixtures are embraced in the Formula I compounds of the invention. Many of the more active renin inhibitors are provided by compounds having a specific arrangement of stereogenic carbons. Within Formula I, reading from the N terminus to the C terminus (terminating with the diol moiety), the preferred configurations for the asymmetric carbons are as follows: RS,RS,S,S,S,R,S.

Compounds of Formula I have been found to inhibit renin and thus limit the production of angiotensin I which, in turn, limits the production of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula 1.

These compounds can be formulated into pharmaceutically-acceptable dosage forms by any of a number of well-known carriers or diluents. The compounds can be formulated using pharmacologically-acceptable acid addition salts and can be used in a suitable hydrated form. The formulated compounds can be administered in oral dosage forms such as tablets, capsules, pills, powders, or granules. The compounds can also be administered intramuscularly, using forms known to the pharmaceutical art. In general, the preferred form of administration is oral. A therapeutically effective but non-toxic quantity of the compound is employed in treatment of high blood pressure in mammals. The dosage regimen for preventing or treating hypertension with the compounds of Formula I is selected upon consideration of a variety of factors, including the type, age, weight, sex, and medical condition of the patient, the severity of the hypertension, the route of administration, and the particular compound employed. Dosages of the compounds are ordinarily in the range from about 0.5 to about 100 mg/kg (active compound-to-body weight), and preferably from about 1.0 to about 20 mg/kg given orally or by injection.

Compounds of Formula I are also useful as diagnostic agents for identification of hypertension due to renin excess.

Compounds of Formula I can be administered as prodrugs. Preferably, esterification of one or more of the hydroxyl groups of the compounds of Formula I is accomplished with amino acids to make aminoesters, succinates to make succinic acid esters, alkanoic acids to make carboxylic acid esters such as valerates, or phosphates to make phosphoric acid esters. Aminoesters and valerates of the Formula I compounds are more preferred.

Procedures for preparation of compounds of Formula I are set forth in the schemes and descriptions under General Synthetic Schemes I & II taken with the specific procedures described in Examples 1–18 which follow thereafter. The substituents A, X and R through R z are as described above for the Formula I substituents.

GENERAL SYNTHETIC SCHEMES I & II

A suitably protected amino aldehyde 1 (Scheme 1) is treated with a Grignard reagent, preferably vinylmagnesium bromide to obtain vinyl carbinol 2. This material, suitably protected, is oxidized, preferably with ozone, followed by dimethyl sulfide treatment to give 3. This aldehyde is reacted with an organometallic reagent such as isobutylmagnesium chloride to give compound 4. This intermediate is deprotected then coupled, using standard amide/peptide coupling methodology, to either alpha or beta amino acid derivatives, suitably protected, to give compound 5. This intermediate is deprotected then coupled, using standard amide/peptide coupling methodology, to intermediate 9 (shown in Scheme II) to give renin inhibitor 6. Synthetic Scheme II shows synthetic routes to intermediate 9, using the reaction of intermediates 7 and 8 followed by deprotection. The synthesis of various types of intermediates 8 (shown more explicitly as intermediates 11, 13 and 15) is depicted, depending on whether X is O, CH$_2$ or NHR$_{10}$. If X=O, a suitably protected lactic acid derivative is treated with phosgene or carbonyl diimidazole to give intermediate 11. If X=CH$_2$, a suitably protected succinic acid derivative is activated by treatment with base/isobutylchloroformate or other standard activating agent to give intermediate 13. If X=NHR$_{10}$, a suitably protected amino acid derivative is activated by treatment with phosgene or other activating agent to give intermediate 15.

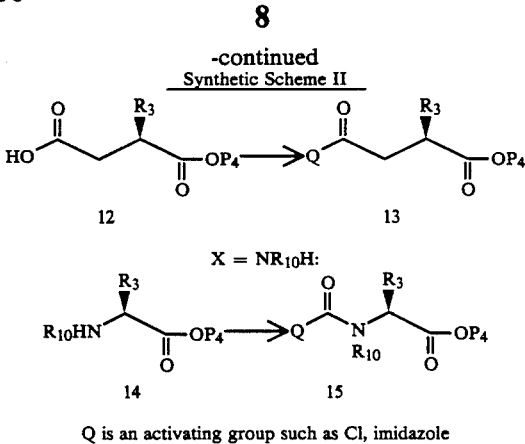

Q is an activating group such as Cl, imidazole

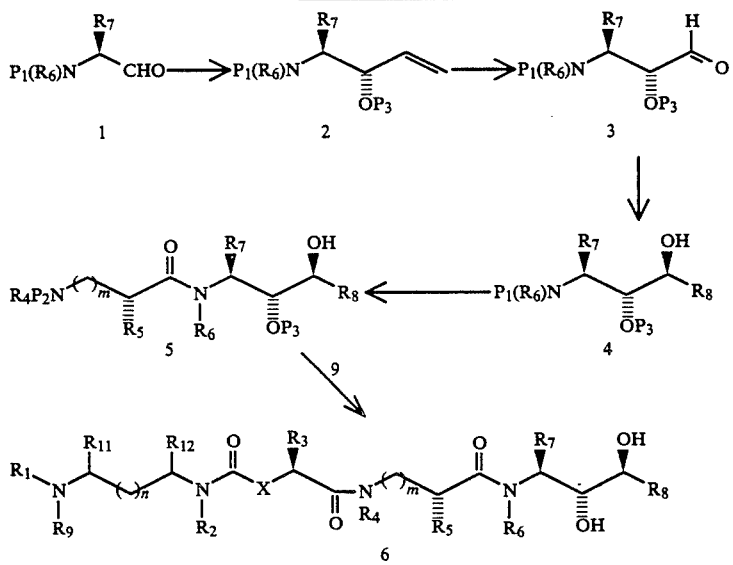

P$_1$ is an N—protecting group
P$_2$ is H or N—protecting group
P$_3$ is H or oxygen protecting group

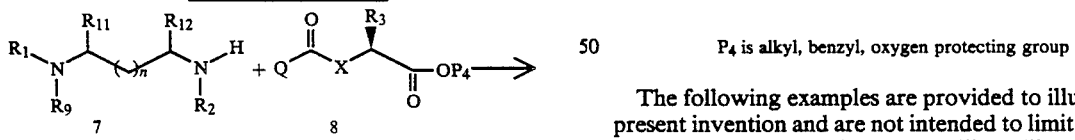

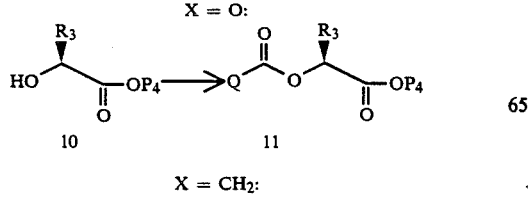

P$_4$ is alkyl, benzyl, oxygen protecting group

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees Centigrade. Within the foregoing synthetic description and examples which follow, abbreviations have meanings as indicated below:

BOC = butyloxycarbonyl
i-Bu = isobutyl
Leu = leucine
Ac = acyl
Me = methyl
TFA = trifluoroacetic acid
THF = tetrahydrofuran
im = imidazole

EXAMPLE 1

(3S,4S)-N-(tert-Butyloxy)carbonyl]-4-amino-3-acetoxy-5-phenylpentene

The preparation of the above intermediate was carried out using the procedure described in Hanson, et al., (1985) J. Org. Chem. 50, 5399.

EXAMPLE 2

(2R,3S)-N-[(tert-Butyloxy)carbonyl]-3-amino-2-acetoxy-4-phenylbutanal

The preparation of the above intermediate was carried out as described in Hanson, et al. above. Ozone/oxygen was bubbled at −70° into a solution of 2.55 g (8.0 mmol) of the allylic acetate of Example 1 in 100 mL of methylene chloride until a deep blue color persisted. Oxygen was introduced until the blue color completely faded, then 3.0 mL of Me$_2$S was added and the solution was allowed to warm to 0-5° and stand overnight. The solvent was removed at 0° under vacuum yielding the title compound as a thick yellow oil which was used in the following step without purification.

EXAMPLE 3

(2S,3R,4S)-N-[(tert-Butyloxy)carbonyl]-2-amino-1-phenyl-3,4-dihydroxy-6-methylheptane The oil prepared in Example 2 was dissolved under nitrogen in 100 mL of dry THF and cooled to −70°. To this solution was added 13 mL (26 mmol) of a 2.0 M solution of isobutylmagnesium chloride in ether and the stirred mixture was allowed to warm to room temperature and stir for 2 hrs. After decomposition with MeOH/H$_2$O the mixture was diluted with ether, washed with saturated NH$_4$Cl solution twice, then dried and the solvents stripped off under vacuum. The residue was allowed to stand overnight in 80% MeOH-H$_2$O containing excess ammonium hydroxide. The MeOH was stripped off and the mixture wa extracted with ether. These extracts were combined, washed with water, dilute KHSO$_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134–136°, Rf (ether): single spot, 0.6. By chromatography of the mother liquors and crystallization of the appropriate fractions, an additional 0.22 g of product, mp 138–139°, was obtained. Anal: Calc'd. for C$_{19}$H$_{31}$NO$_4$ (337.45): C, 67.62; H, 9.26; N, 4.15. Found: C, 67.51; H, 9.43; N, 4.24.

EXAMPLE 4

(2S,3R,4S)-N-[(tert-Butyloxy)carbonyl]-2-amino-1-cyclohexyl-3,4-dihydroxy-6-methylheptane The diol of Example 3, 0.27 g, was reduced in MeOH with 60 psi H$_2$ at 60° in 3 hrs using 5% Rh/C catalyst. After filtering, the solvent was stripped off and the white crystals were recrystallized from CH$_2$Cl$_2$-hexane to furnish tiny needles of the title compound, 0.19 g, mp 126–128°; further recrystallization gave mp 128.5–129.5°. Rf (ether): single spot, 0.8. Anal: Calc'd. for C$_{19}$H$_{37}$NO$_4$(343.50): C, 66.43; H, 10.86; N, 4.08. Found: C, 66.43; H, 11.01; N, 4.03.

EXAMPLE 5

L-Leucineamide of (2S,3R,4S)-2-amino-1-oyclohexyl-3,4-dihydroxy-6-methylheptane

The title compound of Example 4 was treated with trifluoroacetic acid (TFA) for 30 minutes at room temperature and the solvent evaporated. The residue was neutralized with aqueous potassium carbonate and the free amine was extracted with ethyl acetate. This amine was then coupled to Boc-L-leucine-OH following the general procedure given in Example 6. The resulting amide was treated with TFA for 30 minutes at room temperature and the solvent evaporated. The residue was neutralized with aqueous potassium carbonate and the mixture extracted with ethyl acetate. After evaporation, the title free base was obtained: Rf=0.45 (single spot, 9:1 methylene chloride-MeOH, silica); 400 MHz $^1$H NMR (DMSO) spectrum: consistent with structure. Anal: Calc'd. for C$_{20}$H$_{40}$N$_2$O$_3$+0.5 H$_2$O: C, 65.70; H, 11.31; N, 7.67. Found: C, 65.62; H, 11.01; N, 7.49.

EXAMPLE 6

Boc-(im-Tosyl)-L-histidineamide of (2S,3R,4S)-2-amino-1-cyclohexyl-3,4-dihydroxy-6-methylheptane To a stirred solution of N-Boc-(im-tosyl)-L-histidine (809 mg, 1.6 eq) in methylene chloride(5 ml) cooled with an ice/salt bath was added N-methylpiperidine (0.240 ml, 1.6eq) followed by isobutylchloroformate (0.224 ml, 1.4eq). After 5 minutes, the free base (300 mg, 1.23mmol), which had been previously formed by treating the title compound of Example 4 with trifluoroacetic acid followed by potassium carbonate as described in Example 5, dissolved in methylene chloride (5 mL) was added and the reaction mixture was stirred at 0° overnight ca. 15 h. The methylene chloride was evaporated in vacuo to afford an oily residue which was partitioned between ethyl acetate and saturated sodium bicarbonate. The organic layer was separated and further washed with KHSO$_4$solution (1 M) followed by NaHCO$_3$ (1 M). The ethyl acetate layer was dried (MgSO$_4$) and evaporated in vacuo to afford a white solid, which was recrystallized from methanol/diethyl ether. This gave the title compound; (560 mg, 72% yield), 300 MHz $^1$H NMR was fully consistent with the proposed structure. Anal: Calc'd. for C$_{32}$H$_{50}$O$_7$N$_4$S +0.75 H$_2$O: C, 59.28; H, 8.01; N, 8.64. Found: C, 59.31; H, 7.98; N, 8.63.

EXAMPLE 7

(im-Tosyl)-L-histidineamide of (2S,3R,4S)-2-amino-1-cyclohexyl-3,4-dihydroxy-6-methylheptane To a stirred solution of the title compound of Example 6 (3.78 g, 5.96 mmol) in methylene chloride (20 mL) and methanol (5 mL) was added trifluoroacetic acid (25 mL). The reaction mixture was stirred at room temperature for 30 min and then poured onto saturated sodium bicarbonate solution. The solution was adjusted to pH>12 by addition of potassium carbonate and then extracted with ethyl acetate. The organic extracts were dried (MgSO$_4$), and evaporated to afford a solid white residue. Recrystallization from methanol/diethyl ether gave the title compound; (2.8 g, 88% yield); 300 MHz $^1$H NMR spectrum: consistent with the proposed structure. Anal: Calc'd. for C$_{27}$H$_{42}$N$_4$O$_5$S +0.7 H$_2$O: C, 59.25; H, 7.99; N, 10.24. Found: C, 59.29; H, 7.75; N, 10.15.

EXAMPLE 8

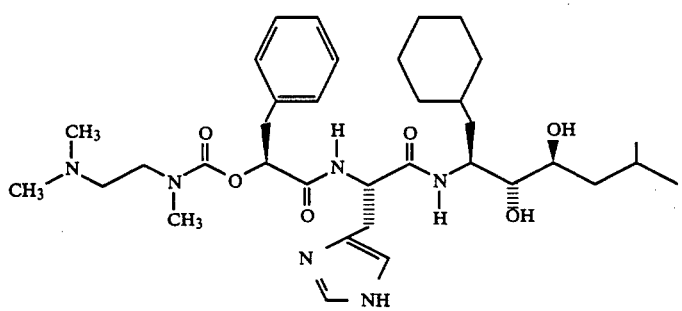

O-{N-[2-N,N-dimethylamino)ethyl]-N-methylaminocarbonyl}-3-L-phenyllactyl-L-histindineamide of (2S,3R,4S)-2-amino-1-cyclohexyl-3,4-dihydroxy-6-methylheptane To a stirred solution of 0-(N-(dimethylaminoethyl)-N-methylaminocarbonyl)-3-L-phenyllactic acid (220 mg, 0.75 mmol) the title compound of Example 14] in methylene chloride (5 mL) in an ice/salt bath was added N-methylpiperidine (0.10 ml, 0.82 mmol) followed by isobutylchloroformate (94 mg, 0.69 mmol). After 5 min, the title compound of Example 7 (390 mg, 0.69 mmol) in methylene chloride (5 ml) was added and the reaction mixture was stirred at 0° for ca 15 h. The methylene chloride was evaporated in vacuo to afford an oily residue which was partitioned between ethyl acetate and saturated aqueous sodium bicarbonate. The organic layer was separated and dried (MgSO4). After evaporation, the crude residue was dissolved in methanol (4 mL) and potassium hydroxide solution (1 mL, 1 M) was added. The reaction mixture was stirred for 30 min, evaporated to dryness and the residue extracted into ethyl acetate. The organic extracts were washed with water, citric acid (1 M) and saturated aqueous sodium bicarbonate solution and dried over MgSO4. Evaporation of the solvent gave a yellow residue which was purified by chromatography on silica (eluting with; methylene chloride/methanol-NH3 (15:85)) to afford the title compound; (60 mg, 14% yield). Anal: Calc'd. for $C_{35}H_{56}N_6O_6 + 2.5 H_2O$: C, 59.89; H, 8.76; N, 11.97. Found: C, 59.78; H, 8.43; N, 11.85. 300 MHz $^1H$ NMR was consistent with the proposed structure.

EXAMPLE 9

O-(N-(N-methyl-N-Boc-aminoethyl)-N-methylaminocarbonyl)-3-L-phenyllactyl-L-(im-tosyl)-histidineamide of (2S,3R,4S)-2-amino-1-cyclohexyl-3,4-dihydroxy-6-methylheptane To a solution of 0-(N-(N-methyl-N-Boc-aminoethyl)-N-methylaminocarbonyl)-3-L-phenyllactic acid (355 mg, 0.93 mmol) in methylene chloride (2 mL) was added N-methylpiperidine (101 mg) in methylene chloride (1 mL). This solution was cooled to 0° and isobutylchloroformate (132 mg) in methylene chloride (1 mL) was added. After 8.5 minutes, the title compound of Example 7 (500 mg, 0.94 mmol) was added as a solid in one portion. The mixture was allowed to stand at 0-4° for 50 hours and then evaporated. The residue was taken up in ethyl acetate and washed with water, followed by 0.5M citric acid (3×20 mL), 5%NaHCO3 (3×20 mL), brine, dried (Na2SO4) and evaporated to give the title compound as an off-white foam: 612 mg (73% yield). Anal: Calc'd. for $C_{46}H_{68}N_6O_{10}S + 0.25 H_2O$: C, 61.27; H, 7.65; N, 9.32. Found: C, 60.96; H, 7.61; N, 8.98. 200 MHz $^1H$ NMR was consistent with proposed structure.

EXAMPLE 10

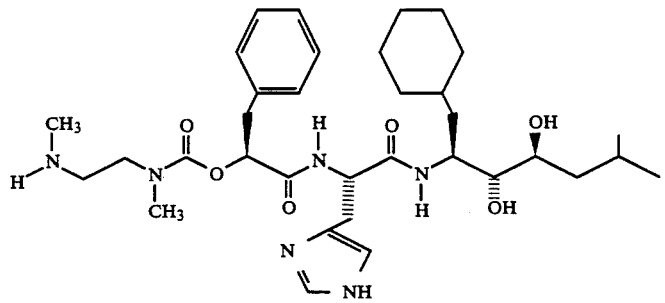

O-N-[2-(N-methylamino)ethyl]-N-methylaminocarbonyl-3-L-phenyllactyl-L-histidineamide of (2S,3R,4S)-2-amino-1-cyclohexyl-3,4-dihydroxy-6-methylheptane The title compound of Example 9 (577 mg) was dissolved in methylene chloride (2 mL) and trifluoroacetic acid (8 mL) was added. The solution was allowed to stand at room temperature for 25 min, then evaporated to an oil. To this was added ethyl ether and the mixture evaporated to form a white, hygroscopic foam. A portion of this foam (300 mg) was dissolved in methanol (2 mL) and 1N aqueous KOH (1.5 mL) was added. The solution was stirred at room temperature for 25 min and the methanol was then evaporated. The mixture was extracted with methylene chloride and the extracts washed with water, dried (Na$_2$SO$_4$) and evaporated to yield a foam (140 mg). A sample was chromatographed on silica gel (eluting with methylene chloride-methanol containing ammonia, 80/20) to give pure title compound Anal: Calc'd. for C$_{34}$H$_{54}$N$_6$O$_6$+2 H$_2$O: C, 60.15; H, 8.61; N, 12.37. Found: C, 60.15; H, 8.26; N, 12.24. 200 MHz $^1$H NMR was consistent with proposed structure.

EXAMPLE 11 rated and the residue partitioned between ether and KHCO$_3$ and the organic layer was dried (MgSO$_4$) and evaporated to give 11.6 g title compound (58% yield). 300 MHz $^1$H NMR was consistent with proposed structure.

EXAMPLE 13

O-(N-(N-methyl-N-Boc-aminoethyl)-N-methylaminocarbonyl)-3-L-phenyllactic acid

At room temperature methyl L-3-phenyllactate (5.7 g) was dissolved in tetrahydrofuran (202 mL) and to this was added carbonyl diimidazole (5.5 g). The mixture

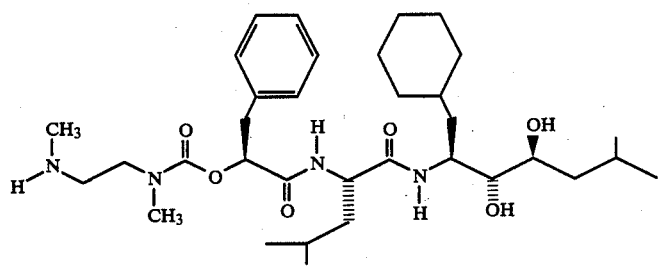

O-{N-[2-(N-methylamino)ethyl[-N-methyl-aminocarbonyl}-3-L-phenyllactyl-L-leucineamide of (2S,3R,4S)-2-amino-1-cyclohexyl-3,4-dihydroxy-6-methylheptane A solution of 0-(N-(N-methyl-N-Boc-amino-ethyl)-N-methylaminocarbonyl)-3-L-phenyllactic acid [Example 13](268 mg) and N-methylpiperidine (69 mg) in methylene chloride (2 mL) was cooled to 0° and isobutylchloroformate (91 mg) was added. This solution was stirred at 0° for 8 minutes, then a solution of the title compound of Example 5 (L-leucineamide of (2S,3R,4S)-2-amino-1-cyclohexyl-3,4-dihydroxy-6-methylheptane, 238 mg) in methylene chloride (2 mL) containing methanol (0.25 mL) was added. This mixture was stirred at 0° for 3 hours and room temperature for 8 hours, then evaporated. The residue was dissolved in methanol and treated with 1N KOH for 20 min at room temperature, then the methanol was evaporated. The residue was partitioned between water and methylene chloride. The organic layer was evaporated to give a foam (395 mg). This foam with treated with trifluoroacetic acid for 30 minutes at room temperature and the solvent evaporated. The residue was neutralized with aqueous potassium carbonate and the free amine was extracted with ethyl acetate to give the title compound (254 mg). Anal: Calc'd. for C$_{34}$H$_{58}$N$_4$O$_6$+3H$_2$O: C, 60.68. Found: C, 60.63. 200 MHz $^1$H NMR was consistent with proposed structure.

EXAMPLE 12

N-Boc-N,N'-dimethylethylene diamine

N,N'-dimethyl ethylenediamine (8.8 g) was dissolved in 200 ml tetrahydrofuran and to this was added over a 10 min period di-t-butyldicarbonate (4.36 g) in 30 mL tetrahydrofuran. 72 hours later, the solvent was evapowas stirred for 4 hours, then the title amine of Example 12 (7.14 g) was added and the mixture was stirred overnight. The solvent was evaporated and the residue taken up in ether, washing with dilute HCl, water, drying over MgSO$_4$ and evaporating to give an oily ester (12.37 g). This ester was dissolved in methanol (32 mL) and 1.5N NaOH (32 mL) was added and stirred for 15 min. at room temperature. The solution volume was reduced by 50% and water was added followed by washing with ether. The aqueous phase was acidified with 6N HCl, extracted with ethyl acetate and organic layer was washed with brine, dried (Na$_2$SO$_4$) and evaporated to give a pale yellow oil (10.3 g). 300 MHz $^1$H NMR was consistent with proposed structure.

EXAMPLE 14

O-(N-(dimethylaminoethyl)-N-methyl-aminocarbonyl)-3-L-phenyllactic acid

Benzyl L-3-phenyllactate (14.28 g) was dissolved in tetrahydrofuran (357 mL) and to this was added carbonyl diimidazole (9.78 g) and the mixture was stirred at room temperature for 4 hours. N,N,N'-trimethylethylene diamine (6.8 g) was added and the mixture stirred for 8 hours. The solvent was evaporated and the residue taken up in ether and washed with water, dried (MgSO$_4$) and evaporated to give a yellow oil (13 g, 61% yield); 300 MHz $^1$H NMR consistent with proposed structure. This ester was hydrogenated over 4% Pd-C @ 5 psi and room temperature for 3.5 hours in tetrahydrofuran. The title compound was obtained as a white solid (10 g) and recrystallized from methanol. Anal: Calc'd. for C$_{15}$H$_{22}$N$_2$O$_4$+H$_2$O: C, 57.68; H, 7.75; N, 8.98. Found: C, 57.60; H, 7.82; N, 8.94.

EXAMPLE 15

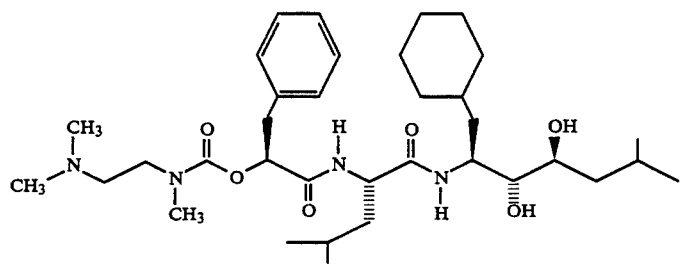

EXAMPLE 15

O-{N-[2-(N,N-dimethylamino)ethyl]-N-methylaminocarbonyl-3-L-phenyllactyl-L-leucineamide of (2S,3R,4S)-2-amino-1-cyclohexyl-3,4-dihydroxy-6-methylheptane O-(N-(dimethylaminoethyl)-N-methyl-aminocarbonyl)-3-L-phenyllactic acid (200 mg) was dissolved in methylene chloride (2 mL), cooled to 0° and treated with isobutylchloroformate (90 mg). The resulting solution was stirred at 0° for 10 minutes, whereupon the title amine of Example 5 (210 mg) was added. The mixture was stirred at 0° for 3 hours and at room temperature for 8 hours. The solvent was evaporated, the residue dissolved in methanol (5 mL) and treated with 1N KOH (0.5 mL) for 10 minutes at room temperature. The methanol was evaporated and the residue extracted with methylene chloride. The organic phase was dried and evaporated to give the title compound as a foam (322 mg, 86% yield). Anal: Calc'd. for $C_{35}H_{60}N_4O_6+0.25$ $H_2O$: C, 65.95; H, 9.56; N, 8.79. Found: C, 65.72; H, 9.76; N, 8.57. 200 MHz $^1H$ NMR was consistent with proposed structure.

EXAMPLE 16

N-Boc-α-(R)-methyl-β-alanineamide of (2S,3R,4S)-2-amino-1-cyclohexyl-3,4-dihydroxy-6-methylheptane To a solution of N-Boc-α-(R,S)-methyl-β-alanine (137 mg, 0.67 mmol) in methylene chloride (4 mL) at −10° C. was added N-methylpiperidine (61 mg, 0.61 mmol) followed by isobutylchloroformate (75 mg, 0.55 mmol). After stirring for 5 min, a solution of (2S,3R,4S)-2-amino-1-cyclohexyl-3,4-dihydroxy-6-methylheptane (101 mg, 0.41 mmol) [prepared from the title compound of Example 4 by treatment with trifluoroacetic acid, followed by aqueous potassium carbonate] in methylene chloride (2 mL) was added. The resulting solution was stirred for 3 hours at -10° C., followed by 2 hours at room temperature at which time a white solid was isolated by filtration (60 mg, 34% yield): Rf=0.3 (5% MeOH/methylene chloride, silica gel); mp 197°-200°; $^1H$ NMR (CDCl$_3$): consistent with proposed structure. Anal: Calc'd. for $C_{23}H_{44}N_2O_5+0.25$ $H_2O$: C, 63.77; H, 10.35; N, 6.46. Found: C, 63.84; H, 10.50; N, 6.45.

EXAMPLE 17

α-(R)-Methyl-β-alanineamide of (2S,3R,4S)-2-amino-1-cyclohexyl-3,4-dihydroxy-6-methylheptane The title compound of Example 16 (53 mg, 0.12 mmol) was stirred with a mixture of trifluoroacetic acid and methanol (9:1, 5 mL). The resulting solution was allowed to stand at room temperature for 20 minutes, then the solvent was evaporated. The resulting oil was stirred for 2 hours with aqueous potassium carbonate (5%, 10 mL). This mixture was then extracted with ethyl acetate which was dried, filtered and evaporated to give the title compound (40 mg, 100%): Rf: 0.10 (5% MeOH/methylene chloride, silica gel). This material was used without further purification.

EXAMPLE 18

O-{N-[2-(N,N-dimethylamino)ethyl]-N-methylaminocarbonyl}-3-L-phenyllactyl-α-(R)-methyl-β-alanineamide of (2S,3R,4S)-2-amino-1-cyclohexyl-3,4-dihydroxy-6-methylheptane O-(N-(dimethylaminoethyl)-N-methylamino-carbonyl)-3-L-phenyllactic acid (the title compound of Example 14) (130 mg, 0.44 mmol) and N-methylpiperidine (49 mg, 0.49 mmol) were dissolved in CH$_2$Cl$_2$ (3.0 mL) and cooled to −10° C. in a salt/ice bath. To this solution was added isobutyl chloroformate (60 mg, 0.44 mmol) in CH$_2$Cl$_2$ (2.0 mL) and the resulting solution was stirred at −10° C. for 5 minutes. Next, a solution of α-(R)-methyl-β-alanineamide of (2S,3R,4S)-2-amino-1-cyclohexyl-3,4-dihydroxy-6-methylheptane (the title compound of Example 17) (136 mg, 0.41 mmol) in 2.5 mL CH$_2$Cl$_2$ was added via pipette, and this solution was stirred at −10° C. for 2 hours followed by 17 hours at 5° C. The solvent was then removed in vacuo and the residue dissolved in ethyl acetate/water. After partitioning, the organic layer was washed twice with 0.5 M Citric acid, twice with saturated NaHCO$_3$ and once with brine. The organics were dried over MgSO$_4$, filtered and the solvent removed in vacuo to yield 174 mg of a yellow oil. Chromatography on silica gel (eluting with 5% CH$_3$OH/CH$_2$Cl$_2$-NH$_3$) afforded 20 mg of a white solid. The NMR is consistent with the assigned structure. Anal: Calc'd. for $C_{33}H_{56}N_4O_6+0.50$ $H_2O$: C: 64.57, H: 9.36, N: 9.12; found C: 64.72, H: 9.33, N: 8.91.

Other compounds of Formula I which can be prepared in accordance with the above-described general and specific procedures are as follows:

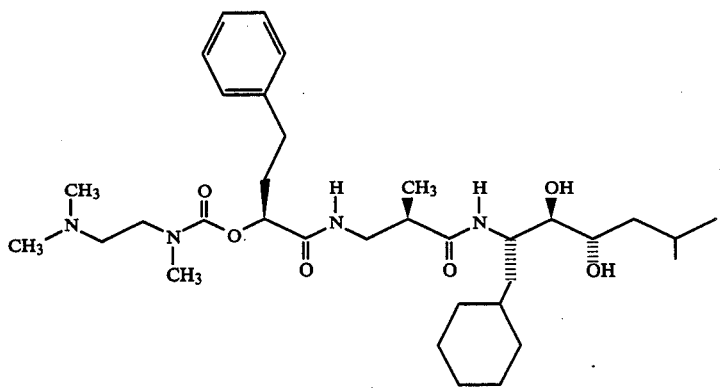

O—{N—[2-(N,N—dimethylamino)ethyl]-N—methylaminocarbonyl}-3-L-homophenyllactyl-α-(R)—methyl-β-alanineamide of (2S, 3R, 4S)—2-amino-1-cyclohexyl-3,4-dihydroxy-6-methylheptane

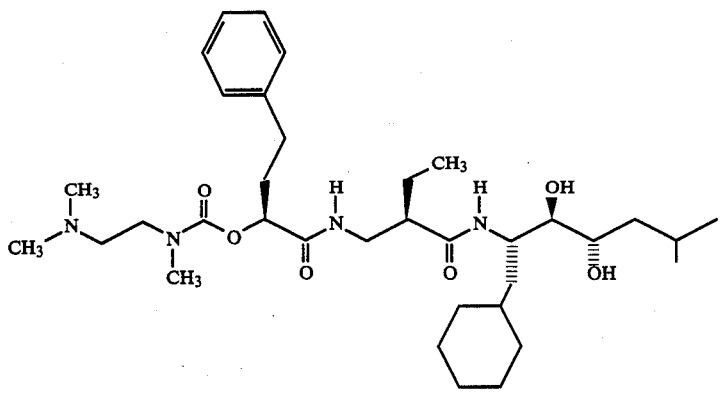

O—{N—[2-(N,N—dimethylamino)ethyl]-N—methylaminocarbonyl}-3-L-homophenyllactyl-α-(R)—ethyl-β-alanineamide of (2S, 3R, 4S)—2-amino-1-cyclohexyl-3,4-dihydroxy-6-methylheptane

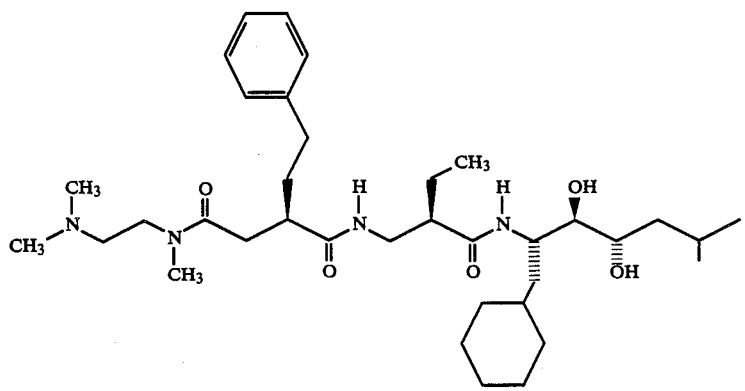

3-{N—[2-(N,N—dimethylamino)ethyl]-N—methylaminocarbonyl}-2-(R)—(2-phenylethyl)-propionyl-α-(R)—ethyl-β-alanineamide of (2S, 3R, 4S)—2-amino-1-cyclohexyl-3,4-dihydroxy-6-methylheptane

BIOLOGICAL EVALUATION

Compounds of Formula I were evaluated as inhibitors of human renin in an in vitro assay, as follows: This human renin inhibition test has been previously described in detail Papaioannou, et al., *Clinical and Experimental Hypertension*, A7(9), 1243–1257 (1985)]. Human renin was obtained from the National Institute for Biological Standards, London. An incubation mixture was prepared containing in a total volume of 0.25 mL 100 mM Tris-acetate buffer at pH 7.4, $25 \times 10^{-6}$ Goldblatt units of renin, 0.05 mL of plasma from human volunteers taking oral contraceptives, 6.0 mM sodium EDTA, 2.4 mM phenylmethyl sulfonyl fluoride, 1.5 mM 8-hydroxyquinoline, 0.4 mg/mL BSA, and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were solubilized in either ethyl alcohol or DMSO and diluted with 100 mM Tris-acetate buffer at pH 7.4 to the appropriate concentration. The final concentration of organic solvent in the reaction mixture was less than 1%. Control incubations at 37° C. were used to correct for effects of organic solvent on renin activity.

Biological Results:

TABLE I

| In Vitro Effect of Compounds on Renin Activity | |
|---|---|
| Compound | Human Renin IC$_{50}$ |
| Example 8 | $1 \times 10^{-9}$ M |
| Example 10 | $1.5 \times 10^{-9}$ M |
| Example 11 | $7.7 \times 10^{-9}$ M |
| Example 15 | $5.4 \times 10^{-9}$ M |

The oral activity of compounds of Formula I was determined in vivo in Marmoset monkeys in accordance with the following procedure: Common marmosets (Callithrix jacchus, Charles River) were placed on a modified high protein low sodium diet (Purina, St. Louis, MO) for 1 to 2 weeks. On the day of the test an animal was anesthetized with isoflurane and cannulated in the femoral artery and vein for blood pressure monitoring, intravenous saralasin infusion and blood sampling. After allowing the animal to recover from surgery for 2 hr, saralasin was infused at 1 microgram/min for 15 minutes to confirm that the animal's blood pressure was dependent on angiotensin 11 levels. The marmoset was allowed to stabilize for 30 min after the saralasin infusion. The test compound was administered orally and blood pressure was monitored for 2 hr. Blood samples were taken in K-EDTA for plasma renin activity before, 30 min, and 1 hr after compound administration. Results are shown in Table II.

TABLE II

| Oral Effect of Compounds on Plasma Renin Activity in Sodium Depleted Marmoset | |
|---|---|
| Compound Tested | % Reduction of Plasma Renin Activity @ 1 h (3 mg/kg dose) |
| Example 8 | 100% |
| Example 10 | 100% |
| Example 11 | 100% |
| Example 15 | 79% |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. O-{N-[2-(N,N-dimethylamino)ethyl]-N-methylaminocarbonyl}-3-L-phenyllactyl-L-histidineamide of (2S,3R,4S)-2-amino-1-cyclohexyl-3,4-dihydroxy-6-methylheptane; or a pharmaceutically-acceptable salt thereof.

2. O-{N-[2-(N-methylamino)ethyl]-N-methylaminocarbonyl}-3-L-phenyllactyl-L-histidineamide of (2S,3R,4S)-2-amino-1-cyclohexyl-3,4-dihydroxy-6-methylheptane; or a pharmaceutically-acceptable salt thereof.

3. A pharmaceutical composition comprising a therapeutically-effective amount of a renin-inhibiting compound and a pharmaceutically-acceptable carrier or diluent, said renin-inhibiting compound selected from the group consisting of O-{N-[2-(N,N-dimethylamino)ethyl]-N-methylaminocarbonyl}-3-L-phenyllactyl-L-histidineamide of (2S,3R,4S)-2-amino-1-cyclohexyl-3,4-dihydroxy-6-methylheptane; or a pharmaceutically-acceptable salt thereof; and O-{N-[2-(N-methylamino)ethyl]-N-methylaminocarbonyl}-3-L-phenyllactyl-L-histidineamide of (2S,3R,4S)-2-amino-1-cyclohexyl-3,4-dihydroxy-6-methylheptane; or a pharmaceutically-acceptable salt thereof.

4. A therapeutic method for treating hypertension, said method comprising administering to a hypertensive patient, or to a patient susceptible to hypertension, a therapeutically-effective amount of a compound selected from the group consisting of O-{N-[2-(N,N-dimethylamino)ethyl]-N-methylaminocarbonyl}-3-L-phenyllactyl-L-histindineamide of (2S,3R,4S)-2-amino-1-cyclohexyl-3,4-dihydroxy-6-methylheptane; or a pharmaceutically-acceptable salt thereof; and O-{N-[2-(N-methylamino)ethyl]-N-methylaminocarbonyl}-3-L-phenyllactyl-L-histidineamide of (2S,3R,4S)-2-amino-1-cyclohexyl3,4-dihydroxy-6-methylheptane or a pharmaceutically-acceptable salt thereof.

* * * * *